United States Patent
Reiley

(10) Patent No.: US 8,110,006 B2
(45) Date of Patent: Feb. 7, 2012

(54) FIBULAR STIFFENER AND BONY DEFECT REPLACER

(75) Inventor: Mark A. Reiley, Piedmont, CA (US)

(73) Assignee: Inbone Technologies, Inc., Berkeley, CA (US)

( * ) Notice: Subject to any disclaimer, the term of this patent is extended or adjusted under 35 U.S.C. 154(b) by 0 days.

(21) Appl. No.: 12/774,854

(22) Filed: May 6, 2010

(65) Prior Publication Data

US 2010/0217402 A1 Aug. 26, 2010

Related U.S. Application Data

(63) Continuation of application No. 11/975,184, filed on Oct. 18, 2007, now abandoned.

(51) Int. Cl.
*A61F 2/42* (2006.01)
(52) U.S. Cl. ..................................................... 623/21.18
(58) Field of Classification Search ............... 623/20.36, 623/21.11–21.19, 20.14, 20.11, 18.11, 16.11, 623/17.11, 17.14, 17.16
See application file for complete search history.

(56) References Cited

U.S. PATENT DOCUMENTS

| | | | | |
|---|---|---|---|---|
| 3,987,500 A * | 10/1976 | Schlein | ...................... | 623/21.18 |
| 4,021,864 A | 5/1977 | Waugh | | |
| 4,232,404 A * | 11/1980 | Samuelson et al. | ........ | 623/21.18 |
| 4,259,072 A | 3/1981 | Hirabayashi et al. | | |
| 4,854,311 A | 8/1989 | Steffee | | |
| 5,098,434 A | 3/1992 | Serbousek | | |
| 5,248,313 A * | 9/1993 | Greene et al. | .................... | 606/62 |
| 5,370,706 A | 12/1994 | Bolesky et al. | | |
| 5,609,595 A * | 3/1997 | Pennig | .......................... | 606/312 |
| 5,766,259 A * | 6/1998 | Sammarco | ................. | 623/21.18 |
| 5,797,899 A | 8/1998 | Tilton, Jr. | | |
| 6,051,751 A * | 4/2000 | Sioshansi et al. | ............. | 128/898 |
| 6,123,710 A * | 9/2000 | Pinczewski et al. | .......... | 606/304 |
| 6,197,029 B1 | 3/2001 | Fujimori et al. | | |
| 6,302,915 B1 * | 10/2001 | Cooney et al. | ............. | 623/21.12 |
| 6,383,223 B1 * | 5/2002 | Baehler et al. | ............. | 623/21.11 |
| 6,527,774 B2 | 3/2003 | Lieberman | | |
| 6,824,567 B2 * | 11/2004 | Tornier et al. | ............... | 623/21.18 |
| 6,860,902 B2 * | 3/2005 | Reiley | ....................... | 623/21.18 |
| 7,708,781 B2 * | 5/2010 | Scheker | ..................... | 623/20.11 |
| 7,722,676 B2 * | 5/2010 | Hanson et al. | ............. | 623/21.12 |
| 7,819,924 B2 * | 10/2010 | VanDer Meulen et al. | .......................... | 623/21.11 |
| 7,875,082 B2 * | 1/2011 | Naidu | ......................... | 623/21.12 |
| 2001/0025199 A1 * | 9/2001 | Rauscher | ................... | 623/21.13 |
| 2002/0143334 A1 | 10/2002 | Hoffmann et al. | | |

(Continued)

FOREIGN PATENT DOCUMENTS

FR 2680968 A1 5/1991

(Continued)

OTHER PUBLICATIONS

International Search Report and Written Opinion issued Apr. 23, 2009, in PCT/US08/080109.

*Primary Examiner* — Alvin J Stewart
(74) *Attorney, Agent, or Firm* — Duane Morris LLP

(57) ABSTRACT

A fibular implant is provided. The implant includes a stem anchored to the fibula and a joint body. The stem is at least partially covered with a bony-in-growth surface. The joint body includes an articulating surface for articulating with the talus. The articulating surface is polished to reduce friction in the ankle joint.

20 Claims, 6 Drawing Sheets

U.S. PATENT DOCUMENTS

| | | |
|---|---|---|
| 2002/0156534 A1 | 10/2002 | Grusin et al. |
| 2003/0120276 A1 | 6/2003 | Tallarida et al. |
| 2003/0216813 A1* | 11/2003 | Ball et al. .................... 623/21.12 |
| 2004/0116932 A1 | 6/2004 | Mazda et al. |
| 2004/0220575 A1 | 11/2004 | Biedermann et al. |
| 2004/0230312 A1* | 11/2004 | Hanson et al. ............. 623/21.12 |
| 2005/0107791 A1 | 5/2005 | Manderson |
| 2005/0119757 A1 | 6/2005 | Hassler et al. |
| 2005/0228388 A1 | 10/2005 | Brodke et al. |
| 2006/0030946 A1* | 2/2006 | Ball et al. .................... 623/21.13 |
| 2006/0074492 A1 | 4/2006 | Frey |
| 2007/0162025 A1 | 7/2007 | Tornier et al. |
| 2007/0198095 A1* | 8/2007 | VanDer Meulen et al. .......................... 623/21.12 |
| 2008/0051912 A1 | 2/2008 | Hollawell |
| 2008/0249577 A1 | 10/2008 | Dreyfuss |
| 2009/0054992 A1* | 2/2009 | Landes et al. .............. 623/21.18 |
| 2009/0099664 A1* | 4/2009 | Forrester .................... 623/21.18 |
| 2009/0182433 A1* | 7/2009 | Reiley et al. .............. 623/18.11 |
| 2009/0240338 A1* | 9/2009 | Reiley ........................ 623/21.18 |
| 2009/0254189 A1* | 10/2009 | Scheker .................... 623/21.11 |
| 2010/0076568 A1* | 3/2010 | Gupta et al. ............... 623/21.12 |
| 2010/0087879 A1* | 4/2010 | Vanasse et al. ............. 606/86 R |

FOREIGN PATENT DOCUMENTS

| | | |
|---|---|---|
| WO | 2006052874 A2 | 5/2006 |

* cited by examiner

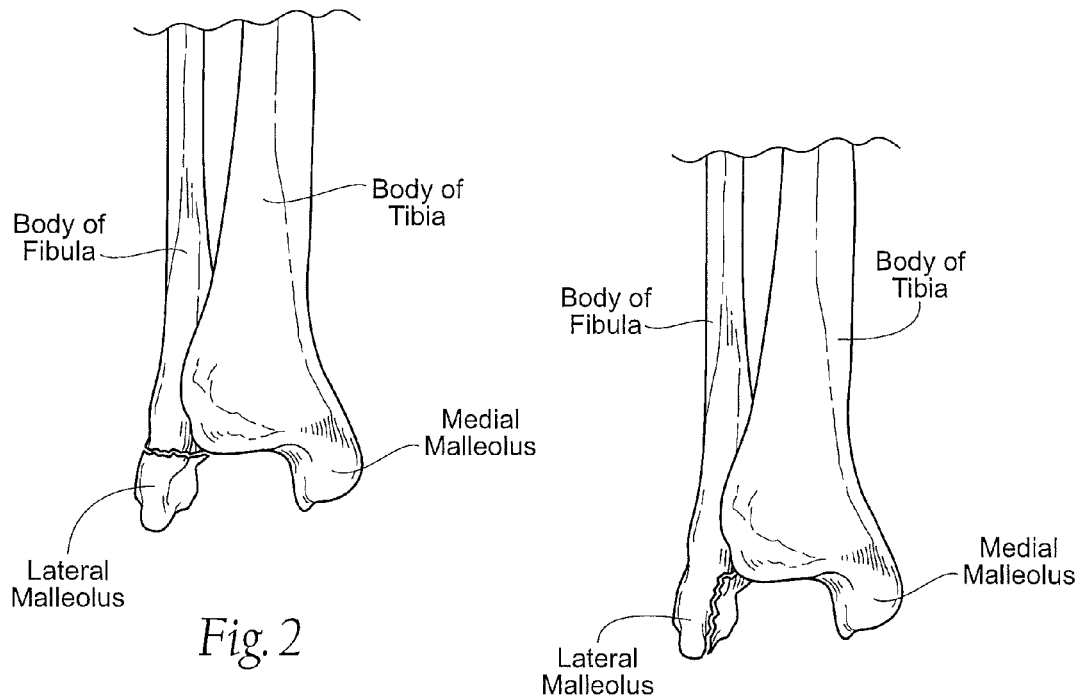
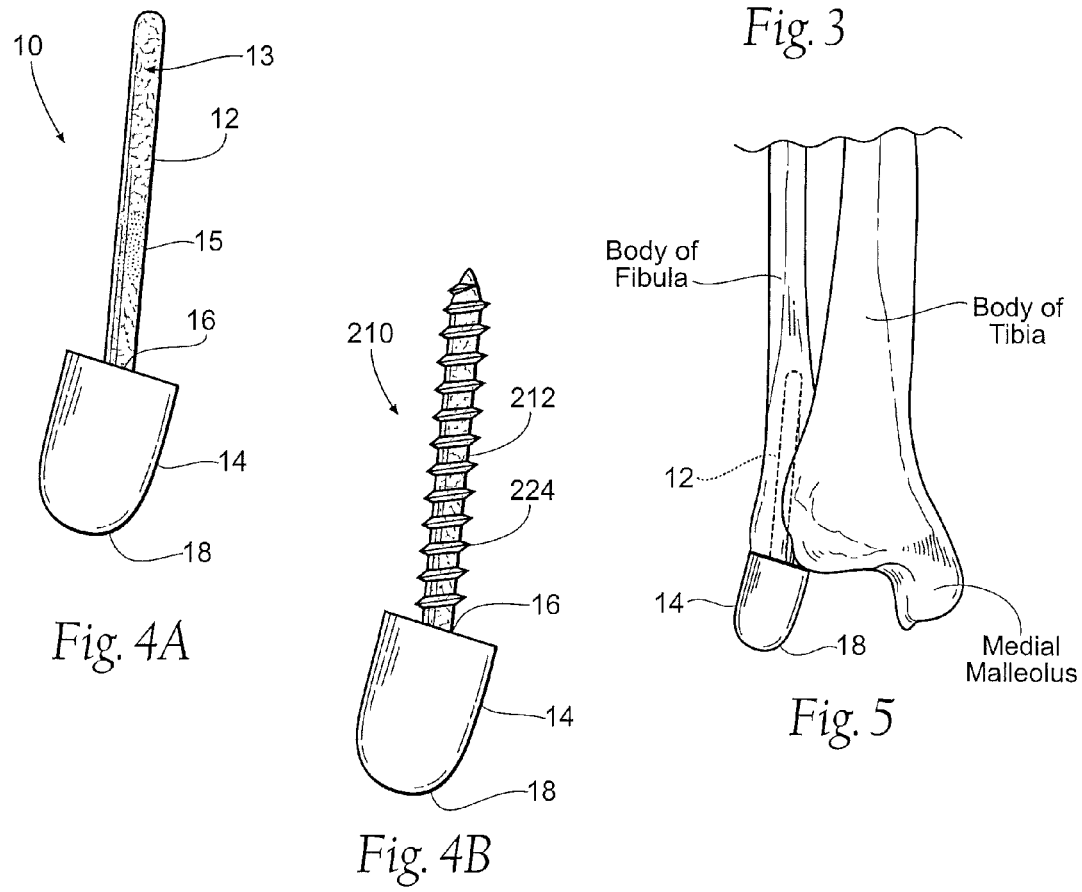

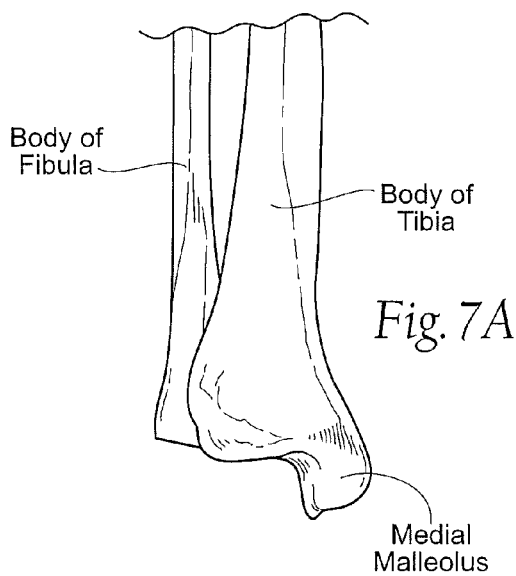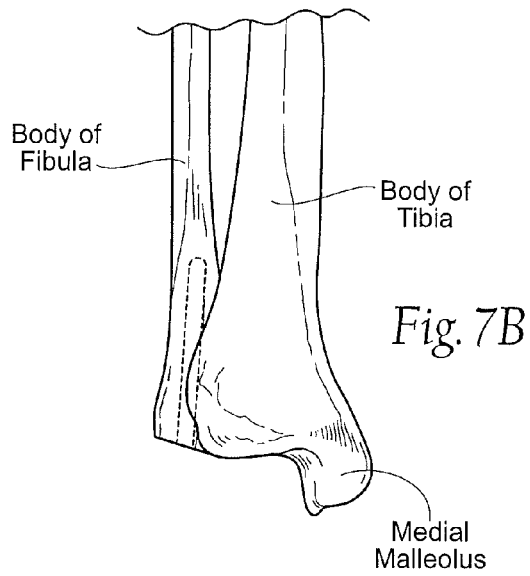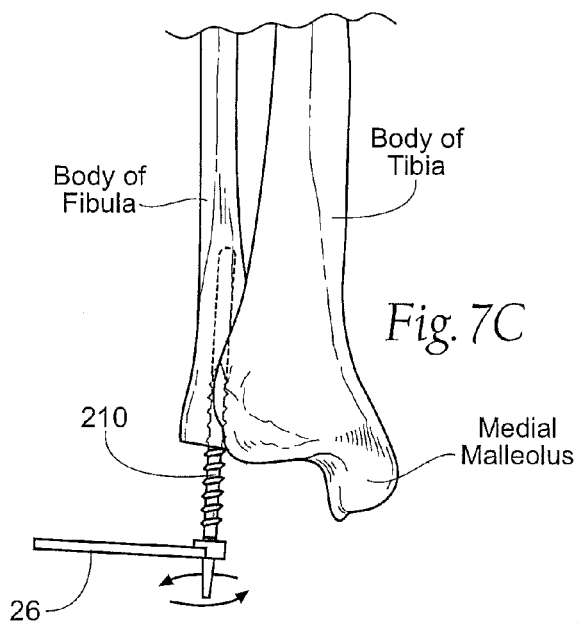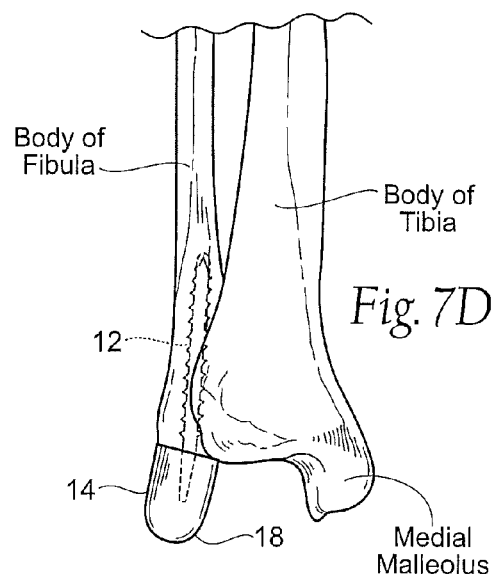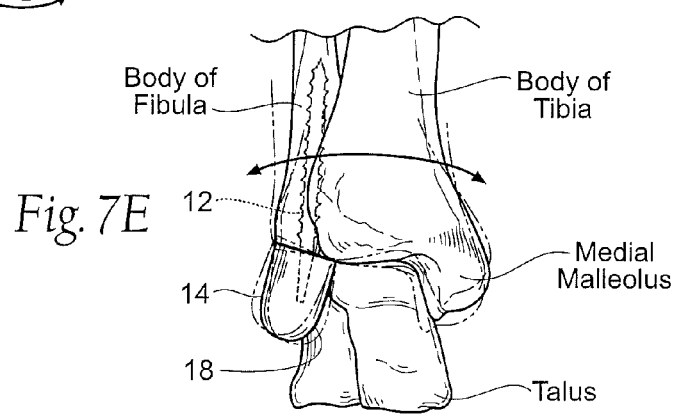

FIBULAR STIFFENER AND BONY DEFECT REPLACER

CROSS-REFERENCE TO RELATED APPLICATIONS

This application is a continuation of U.S. patent application Ser. No. 11/975,184 filed on Oct. 18, 2007, the entirety of which is herein incorporated by reference in its entirety.

FIELD OF THE INVENTION

The invention relates to fibular replacement prostheses, systems, and associated surgical procedures.

BACKGROUND OF THE INVENTION

Many times after trauma, previous ankle surgery where a portion or the entire distal fibula has been removed, or congenital deformity, adequate fibula does not remain to perform a desired operation such as a total ankle replacement, ankle ligament repair, or fibular osteotomy correction. Although the fibula does not carry much of the weight in the leg, the distal fibula is required to provide stability to the ankle joint. In these cases it would be useful to have a device which both strengthens the fibula and allows ample support of a replacement piece of the distal fibula, also known as the lateral malleolus.

SUMMARY OF THE INVENTION

The present invention provides devices and methods for stiffening the fibula and replacing a broken lateral malleolus.

The present invention may include an elongate stem for inserting into the fibula and a joint body coupled to the stem member for replacing the lateral malleolus.

The stem may take on various shapes and have various cross sections.

Other objects, advantages, and embodiments of the invention are set forth in part in the description which follows, and in part, will be obvious from this description, or may be learned from the practice of the invention.

BRIEF DESCRIPTION OF THE DRAWINGS

FIG. 2 is an anterior view of the lower leg showing a fractured lateral malleolus where the entire lateral malleolus is broken off.

FIG. 3 is an anterior view of the lower leg showing a fractured lateral malleolus where only a portion of the lateral malleolus is broken off.

FIG. 4A is an anterior view of a lateral malleolus prosthesis according to the presenting invention.

FIG. 4B is an alternate embodiment of the lateral malleolus prosthesis of FIG. 4A.

FIG. 5 is an anterior view of the prosthesis of FIG. 4A implanted in the lower leg of FIG. 2.

FIGS. 7A to 7E show the steps of the insertion of the prosthesis of FIG. 4B into the lower leg of FIG. 2.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

I. Anatomy of the Lower Leg

Figure 1A:
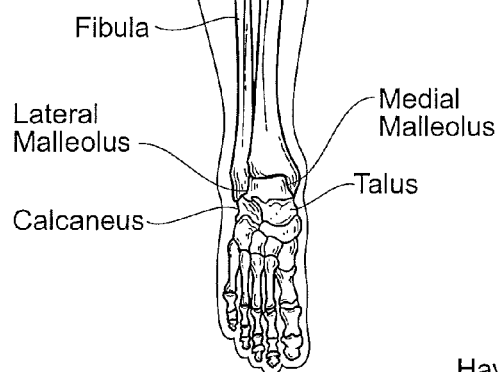
FIG. 1A is an anterior view of a human leg and showing the leg and foot skeleton.

Referring to FIG. 1A, the lower leg comprises the tibia and the fibula. The tibia and the fibula, along with the talus form the ankle joint which allows for the up and down movement of the foot. The subtalar joint, located below the ankle is made of the talus and calcaneous. The subtalar joint allows for side to side movement of the foot.

The distal end of the fibula enlarges to form the lateral malleolus (see FIG. 1A). The distal end of the tibia forms the medial malleolus. The medial malleolus and the lateral malleolus each articulate with the lateral surface of the talus, as FIG. 1A shows. The lateral malleolus of is an important element of the ankle, as it lends stability to the ankle joint. Therefore, it is desirable to replace a damaged lateral malleolus in order to create a stable articulating ankle joint.

Figure 1B:
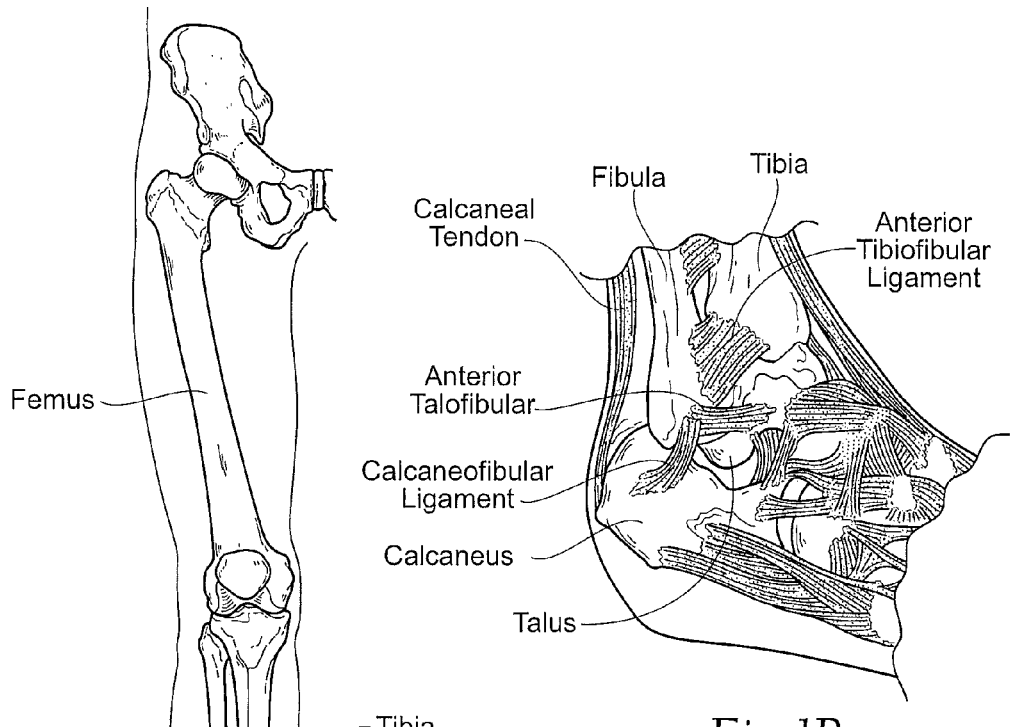
FIG. 1B is a lateral view of a human ankle joint showing the ligaments.

FIG. 1B shows the ligaments on the lateral side of the ankle joint. The major ligaments on the lateral side are the anterior talofibular ligament which connects the fibula to the talus, the anterior tibiofibular ligament which connects the tibia to the fibula and the calcaneofibular ligament which connects the fibular to the calcaneous. These ligaments provide lateral stability to the ankle.

Figure 1C:
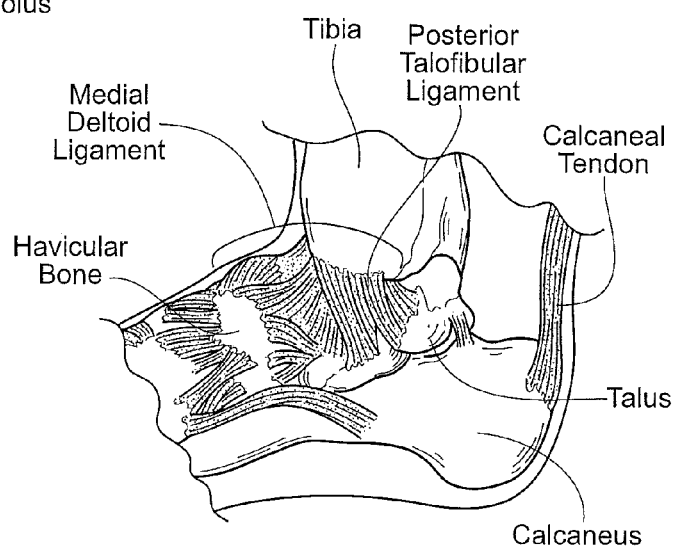
FIG. 1C is a medial view of a human ankle joint showing the ligaments.

FIG. 1C shows the ligaments on the medial side of the ankle joint. The major ligament on the medial side is the medial deltoid ligament which attaches proximally to the medial malleolus and fans out to attach to the talus, calcaneous, and navicular bone. The deltoid muscles provide medial stability to the ankle.

II. Fibular Prosthesis

FIGS. 2 and 3 show examples of a damaged fibula. Fibular fractures commonly occur 2-6 cm proximal to the distal end of the lateral malleolus. The fibula may be damaged due to injury, surgery, or a congenital defect. The fibula may be broken above the lateral malleolus, as shown in FIG. 2, or a portion of the lateral malleolus may be broken off, as shown in FIG. 3.

A. Total Prosthesis

FIG. 4A shows an example of a fibular prosthetic 10 for use in a fracture as shown in FIG. 2, where the entire lateral malleolus is missing. The prosthetic 10 includes a stem 12 and a joint body 14 coupled to the stem 12. The stem 12 reinforces the fibula while the joint body 14 replaces the lateral malleolus.

In one embodiment the stem 12 comprises an elongated body. However, it should be understood that the prosthesis stem 12 can take various forms. The stem 12 may be of any size or shape deemed appropriate by the physician. The stem 12 is desirable selected by the physician taking into account the morphology and geometry of the site to be treated. It should be understood that the stem 12 could be of virtually any width or length, depending upon the size of the patient and his or her bone dimensions. While the stem 12 in the disclosed embodiments has a circular cross-section, it should be understood that the stem 12 could be formed in various other cross-sectional geometries, including, but not limited to, elliptical, polygonal, irregular, or some combination thereof.

The stem 12 may be made of any total joint material or materials commonly used in the prosthetic arts, including, but not limited to metals, ceramics, titanium, titanium alloys, tantalum, chrome cobalt, surgical steel, or any other total joint replacement metal and/or ceramic, bony in-growth surface, sintered glass, artificial bone, any uncemented metal or ceramic surface, or a combination thereof.

It may be desirable to provide surface texturing 13 along at least a portion of the length of the stem 12 to promote bony in-growth on its surface (see FIG. 4A). The surface texturing 13 can comprise, e.g., through holes, and/or various surface patterns, and/or various surface textures, and/or pores, or combinations thereof. The stem 12 can be coated or wrapped or surfaced treated to provide the surface texturing 13, or it can be formed from a material that itself inherently possesses a surface conducing to bony in-growth, such as a porous mesh, hydroxyapetite, or other porous surface.

If desired, the stem 12 may further be covered with one or more coating 15 such as antimicrobial, antithrombotic, and osteoinductive agents, or a combination thereof (see FIG. 4A). Any of these coatings 15 may be used in conjunction with surface texturing, if desired. Alternatively, the stem 12 may be formed from a suitable biological material, or a combination of metal and biological material, including, but not limited to hydroxyapetate, calcium phosphate, or other biocompatible bony substitutes. The stem 12 could further be covered with biological bone-growth stimulants, e.g., but not limited to bone morphogenic proteins.

The stem 12 may be fixed in the fibula using poly(methylmethacrylate) bone cement, hydroxyapatite, a ground bone composition, screws, or a combination thereof, or any other fixation materials or methods common to one of skill in the art of prosthetic surgery, as is shown in FIGS. 6A to 6D.

Figure 6A:
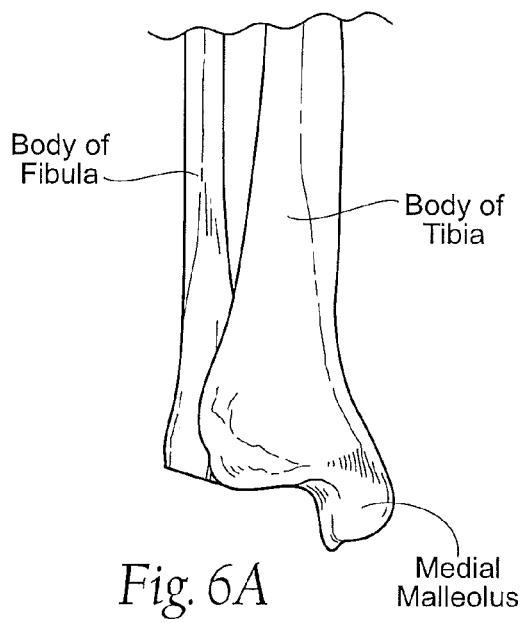
FIGS. 6A to 6D show the steps of the insertion of the prosthesis of FIG. 4A into the lower leg of FIG. 2.

Especially in cases of trauma, where the fracture of the fibula is jagged as shown in FIG. 2, it may be desirable to create a flat surface, such as that shown in FIG. 6A, for prosthetic attachment. A flat surface can be created by using standard surgical tools, such as a surgical saw to cut away a portion of the fibula.

Figure 6B:
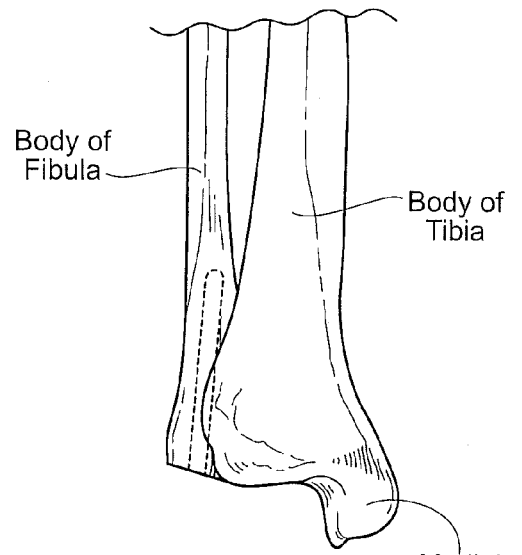
Figure 6C:
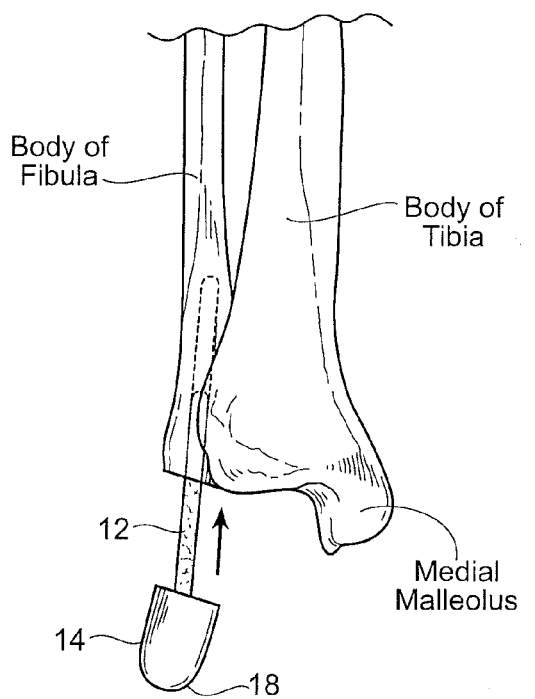

The physician may then use conventional methods to create a bore of the desired size and configuration in the fibula, as shown in FIG. 6B. Preferably, the physician will use a surgical drill sized and configured to create a conical bore similar in size and configuration to the stem 12. The bore is desirable sized and configured to permit tight engagement of the stem 12 within the bore and thereby restrict movement of the stem 12 within the bore. As shown in FIG. 6C, the stem 12 is then inserted into the bore. The pre-formed bore may be slightly smaller than the stem 12, while still allowing the stem 12 to be secured into position within the bore by tapping.

Figure 6D:
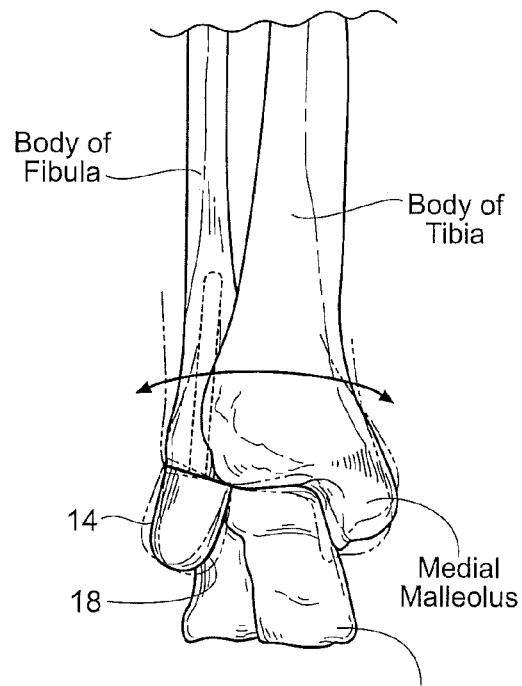

As shown in FIG. 6D, the illustrated embodiment of the joint body 14 has generally the same configuration as a human lateral malleolus. The joint body 14 includes an articulating surface 18 that articulates with the talus to form the ankle joint. The articulating surface 18 of the joint body 14 is preferably made of a polished biocompatible metal or metallic alloy that allows as frictionless an engagement with the talus as possible.

In an alternate embodiment of the fibular stiffener 210 the stem 212 is formed with external screw-like threads 224 along the stem 212 (see FIG. 4B). In this arrangement, the threaded stem 212 can be screwed into a pre-drilled bore in the fibula, as shown in FIGS. 7A to 7E. In inserting the threaded stem, it may be desirable to have the stem and the joint body formed as two separate parts, as will be described in detail below.

As shown in FIG. 2, the fracture may leave a jagged surface on the lateral malleolus. The physician may first use standard surgical tools, such as a bone saw to create a flat surface, such as that shown in FIG. 7A, for prosthetic attachment. The physician may then use a tool such as a surgical drill to create a bore sized and configured to engage the stem 212, as shown in FIG. 7B. As shown in FIG. 7C. The physician may then screw the stem 212 into the preformed bore. A suitable tool 26 may be used to aid in insertion of the stem. Preferably, the diameter of the bore is slightly smaller than diameter of the stem 212 so that the threads 224 on the stem 212 may engage the fibula. The joint body 14 is then attached to the stem 212, as shown in FIG. 7D.

As shown in FIG. 7E, the illustrated embodiment of the joint body 14 has generally the same configuration as a human lateral malleolus. The joint body 14 includes an articulating surface 18 that articulates with the talus to form the ankle joint. The articulating surface 18 of the joint body 14 is preferably made of a polished biocompatible metal or metallic alloy that allows as frictionless an engagement with the talus as possible.

Figure 8:
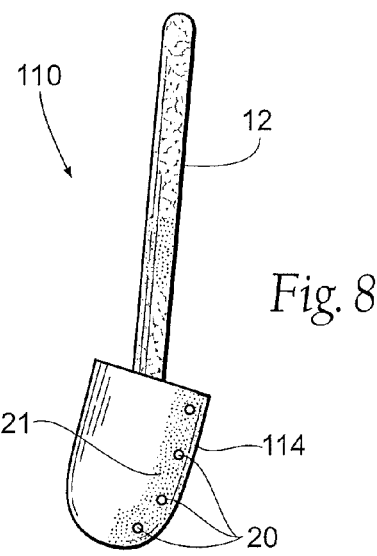
FIG. 8 is an anterior view of an alternate embodiment of a lateral malleolus prosthesis.

In some cases it may be desirable to allow for ligament attachment to the prosthesis. FIG. 8 shows an alternative joint body 114 which may therefore further be formed with holes 20 therethrough. These holes 20 may be used to facilitate ligament attachment. For example, sutures may be passed through the holes 20 and through the ligaments to attach the ligaments to the joint body 114. At least a portion of the joint body 114 may be covered with biologic surfaces 21, as shown in FIG. 8 to enable ligament reattachment.

Figure 9:
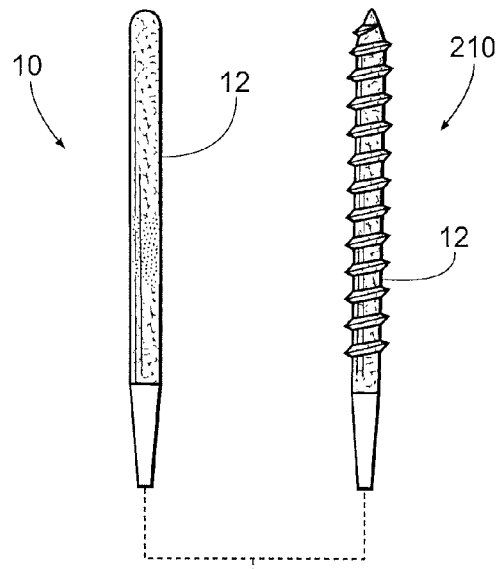
FIG. 9 is a side view showing examples of the various interchangeable components of the lateral malleolus prosthesis of the present invention.

As shown in FIG. 9, as described above, the stem 12 and joint body 14 can be formed as a single unit, or as a multi-component prosthesis. The distal end of the stem 12 may having interlocking components, common to those of skill in the art to allow other components of the prosthetic body to lock into the stem 12. For example, as shown in FIG. 9, the end of the stem may be formed with a Morse Taper. In this manner, the treating physician may choose an appropriately sized and configured stem 12 or 212, and an appropriately sized and configured joint body 14, 114, or 214 based on the patent's anatomy and the particular configuration of the damaged fibula.

B. Partial Prosthesis

Figure 10A:
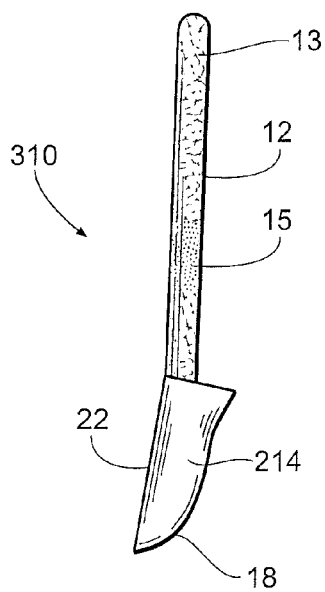
FIG. 10A is an anterior view of an additional alternate embodiment of a lateral malleolus prosthesis.

FIG. 10A shows an example of a prosthetic 210 for use in a fracture as shown in FIG. 3 where only a portion of the lateral malleolus is missing. The prosthetic 210 includes a stem 12 as described above and a partial joint body 214. The partial joint body 214 is designed to have a portion that engages the fibula and a portion that articulates with the talus to form the ankle joint.

Figure 10B:
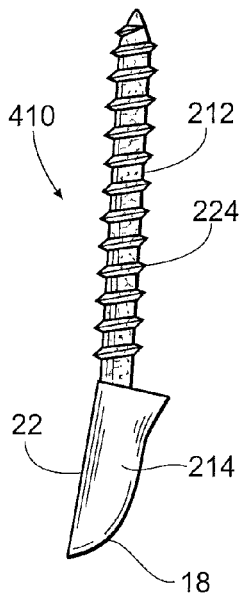
FIG. 10B is an alternate embodiment of the lateral malleolus prosthesis of FIG. 10A.
Figure 11:
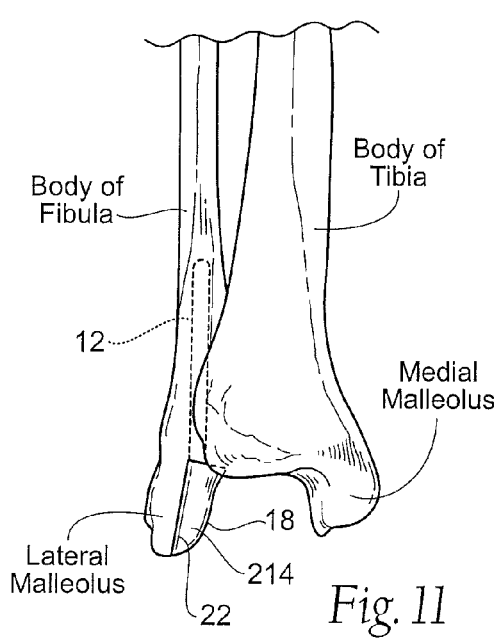
FIG. 11 is an anterior view the prosthesis of FIG. 10A implanted in the lower leg of FIG. 3.

In the illustrated embodiment of FIG. 10A, the stem 12 comprises an elongated body. However, it should be understood that the prosthesis stem 12 can take various forms. For example, as shown in FIG. 10B, the stem 212 may be formed with external threads along the body of the stem.

The stem 12 may be of any size or shape deemed appropriate by the physician. The stem 12 is desirable selected by the physician taking into account the morphology and geometry of the site to be treated. It should be understood that the stem 12 could be of virtually any length or width, depending upon the size of the patient and his or her bone dimensions. While the stem 12 in the disclosed embodiments has a generally circular cross-section, it should be understood that the stem 12 could be formed in various other cross-sectional geometries, including, but not limited to, elliptical, polygonal, irregular, or some combination thereof.

The stem 12 may be made of any total joint material or materials commonly used in the prosthetic arts, including, but not limited to metals, ceramics, titanium, titanium alloys, tantalum, chrome cobalt, surgical steel, or any other total joint replacement metal and/or ceramic, bony in-growth surface, sintered glass, artificial bone, any uncemented metal or ceramic surface, or a combination thereof.

It may be desirable to provide surface texturing 13 along at least a portion of the length of the stem 12 to promote bony in-growth on its surface (see FIG. 10A). The surface texturing 13 can comprise, e.g., through holes, and/or various surface patterns, and/or various surface textures, and/or pores, or combinations thereof. The stem 12 can be coated or wrapped or surfaced treated to provide the surface texturing 13, or it can be formed from a material that itself inherently possesses a surface conducing to bony in-growth, such as a porous mesh, hydroxyapetite, or other porous surface.

If desired, the stem 12 may further be covered with one or more coatings 15 such as antimicrobial, antithrombotic, and osteoinductive agents, or a combination thereof (see FIG. 10A). Any of these coatings 15 may be used in conjunction with surface texturing, if desired. Alternatively, the stem 12 may be formed from a suitable biological material, or a combination of metal and biological material, including, but not limited to hydroxyapetate, calcium phosphate, or other biocompatible bony substitutes. The stem 12 could further be covered with biological bone-growth stimulants, e.g., but not limited to bone morphogenic proteins.

The stem 12 may be fixed in the fibula using poly(methylmethacrylate) bone cement, hydroxyapatite, a ground bone composition, screws, or a combination thereof, or any other fixation materials or methods common to one of skill in the art of prosthetic surgery.

Figure 12A:
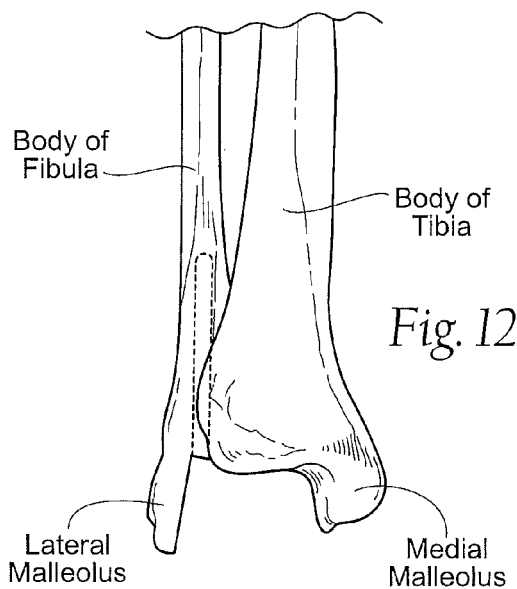
FIGS. 12A to 12D show the steps of the insertion of the prosthesis of FIG. 10A implanted in the lower leg of FIG. 3.

Especially in cases of trauma, where the fracture of the fibula is jagged as shown in FIG. 3, it may be desirable to create a flat surface, such as that shown in FIG. 12A for prosthetic attachment. A flat surface can be created by using a surgical saw to cut away a portion of the fibula.

Figure 12B:
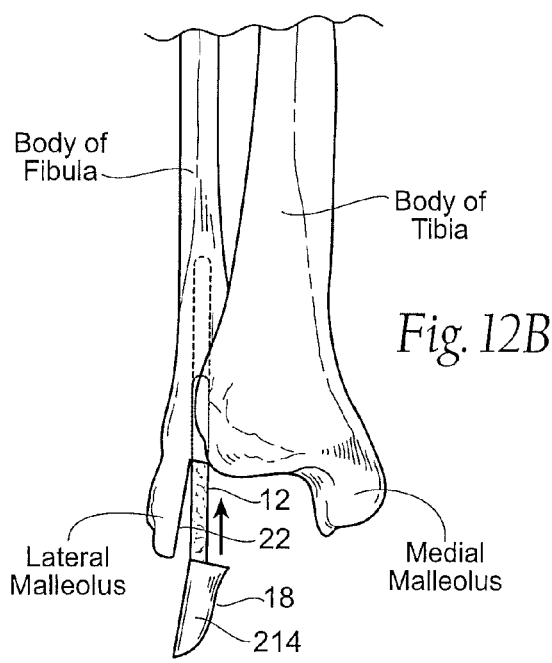
Figure 12C:
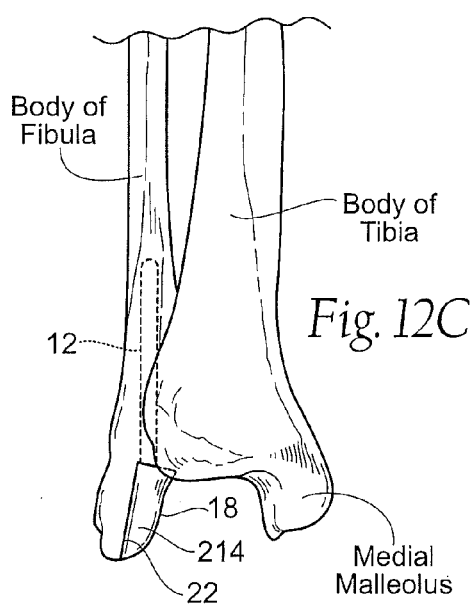
Figure 12D:
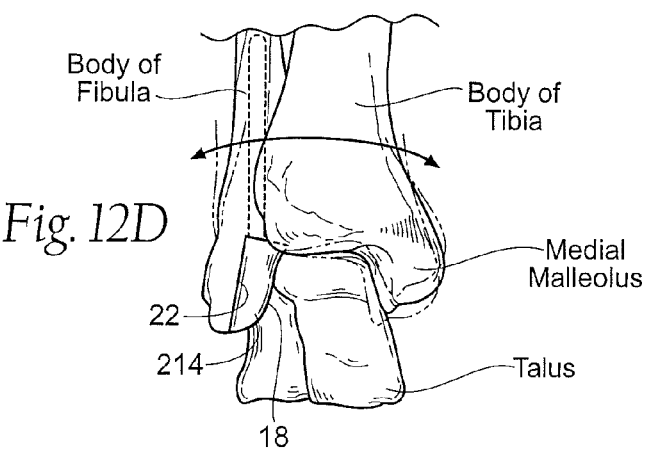

The physician may then use conventional methods to create a bore of the desired size and configuration in the fibula, as shown in FIG. 12A. Preferably, the physician will use a surgical drill sized and configured to create a conical bore similar in size and configuration to the stem 12. The bore is desirable sized and configured to permit tight engagement of the stem 12 within the bore and thereby restrict movement of the stem 12 within the bore. As shown in FIGS. 12B and 12C, the stem 12 of the prosthesis is then inserted into the bore. The stem may be inserted by standard surgical methods. For example, the stem could be inserted by tapping the stem with a surgical tool such as a mallet. The pre-formed bore may be slightly smaller than the stem 12, while still allowing the stem 12 to be secured into position within the bore by tapping. When inserted, the joint body 214 of the prosthesis articulates with the talus, as shown in FIG. 12D.

In an additional alternate embodiment of a fibular stiffener 410 shown in FIG. 10B, the stem 212 is formed with external screw-like threads 224 along the stem 212.

In this arrangement, the threaded stem 212 can be screwed into a pre-drilled bore in the fibula, in the same manner as described above and shown in FIGS. 7A to 7E. In inserting the threaded stem, it may be desirable to have the stem and the joint body formed as two separate parts, as is shown in FIG. 9, and will be described in detail below.

As shown in FIG. 3, the fracture may leave a jagged surface on the lateral malleolus. The physician may first use standard surgical tools, such as a bone saw to create a flat surface, such as that shown in FIG. 12A, for prosthetic attachment. The physician may then use a tool such as a surgical drill to create a bore sized and configured to engage the stem 212, as shown in FIG. 12B.

As shown in FIG. 7C, the physician may then screw the stem 212 into the preformed bore. A suitable tool 26 may be used to aid in insertion of the stem. Preferably, the diameter of the bore is slightly smaller than diameter of the stem 212 so that the threads 224 on the stem 212 may engage the fibula. The joint body 214 is then attached to the stem, as shown in FIG. 12D. The joint body 214 may then articulate with the talus as shown in FIG. 12D.

As shown in FIGS. 10A and 10B, the illustrated embodiment of the joint body 214 has generally the same configuration as the missing portion of a human lateral malleolus. The joint body 214 includes a portion 22 that engages the fibula, on the lateral side of the partial joint body 214. The fibula engaging portion 22 may desirably be formed with a bony-in-growth surface, such as through holes, and/or various surface patterns, and/or various surface textures, and/or pores, or combinations thereof. The fibula engaging portion 22 can be coated or wrapped or surfaced treated to provide the surface texturing, or it can be formed from a material that itself inherently possesses a surface conducing to bony in-growth, such as a porous mesh, hydroxyapetite, or other porous surface. The fibula engaging portion 22 could further be covered with biological bone-growth stimulants, e.g., but not limited to bone morphogenic proteins.

As shown in FIG. 12D, the joint body 214 also includes an articulating surface 18 for engaging the talus. It is desirable that the articulating surface 18 of the partial joint body 214 should be made of a polished biocompatible metal or metallic allow to reduce friction as the prosthesis 210 articulates with the talus.

As shown in FIG. 9, as described above, the stem 12 and joint body 214 may be formed as a single unit, or as a multi-component prosthesis. The distal end of the stem 12 may having interlocking components, common to those of skill in the art to allow other components of the prosthetic body to lock into the stem 12. For example, as shown in FIG. 9, the end of the stem may be formed with a Morse Taper. In this manner, the treating physician may choose an appropriately sized and configured stem 12 or 212, and an appropriately sized and configured joint body 14, 114, or 214 based on the patent's anatomy and the particular configuration of the damaged fibula.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A method, comprising
   removing at least a portion of a lateral malleolus to create a flat on an end of a fibula;
   forming a cavity in the fibula that inwardly extends from the flat in a direction that is substantially parallel to a longitudinal direction of the fibula; and
   inserting an elongate stem of a prosthesis into the cavity in the fibula until a planar first end of a substantially cylindrical joint body abuts the flat and a side of the substantially cylindrical joint body that terminates at a second rounded end is in position to articulate with a talus.

2. The method according to claim 1 further comprising fixing the prosthetic stem in the fibula.

3. The method according to claim 2 wherein the prosthetic stem is fixed in the fibula by screwing the stem into the cavity in the fibula.

4. The method according to claim 1, wherein the stem has a conical configuration.

5. The method according to claim 1, wherein the stem includes a biologic material.

6. The method according to claim 1, wherein the stem includes at least one thread along an exterior surface thereof.

7. The method according to claim 1, wherein the cylindrical joint body and stem are integrally formed.

8. The method according to claim 1, wherein at least a portion of the stem is adapted for bony in-growth.

9. The method according to claim 1, wherein the cylindrical joint body includes a flat surface that extends from the first planar end to the second rounded end.

10. The method according to claim 1, wherein an axis defined by the stem extends from the planar surface at an acute angle.

11. The method according to claim 1, wherein the cylindrical joint body defines at least one hole for facilitating attachment of a ligament to the prosthesis.

12. The method according to claim 1, wherein the stem includes a smooth outer surface.

13. A method, comprising
    removing at least a portion of a lateral malleolus to create a flat on an end of a fibula;
    forming a cavity in the fibula that inwardly extends from the flat in a direction that is substantially parallel to a longitudinal direction of the fibula; and
    screwing an elongate threaded stem of a prosthesis into the cavity in the fibula until a planar first end of a substantially cylindrical joint body abuts the flat and a side of the substantially cylindrical joint body that terminates at a second rounded end is in position to articulate with a talus.

14. The method according to claim 13, wherein the stem has a conical configuration.

15. The method according to claim 13, wherein the stem includes a biologic material.

16. The method according to claim 13, wherein the cylindrical joint body and stem are integrally formed.

17. The method according to claim 13, wherein at least a portion of the stem is adapted for bony in-growth.

18. The method according to claim 13, wherein the cylindrical joint body includes a flat surface that extends from the first planar end to the second rounded end.

19. The method according to claim 13, wherein an axis defined by the stem extends from the planar surface at an acute angle.

20. The method according to claim 13, wherein the cylindrical joint body defines at least one hole for facilitating attachment of a ligament to the prosthesis.

* * * * *